United States Patent [19]

Milberger et al.

[11] 4,218,382

[45] Aug. 19, 1980

[54] PRODUCTION OF MALEIC ANHYDRIDE FROM FOUR-CARBON HYDROCARBONS USING CATALYSTS PREPARED BY WATER REFLUX TECHNIQUES

[75] Inventors: Ernest C. Milberger, Solon; Serge R. Dolhyj, Parma; Noel J. Bremer, Kent, all of Ohio

[73] Assignee: Standard Oil Company, Cleveland, Ohio

[21] Appl. No.: 954,056

[22] Filed: Oct. 23, 1978

[51] Int. Cl.² .................................................. C07D 307/60
[52] U.S. Cl. .................................. 260/346.75; 252/437
[58] Field of Search ..................................... 260/346.75

[56] References Cited

U.S. PATENT DOCUMENTS

| | | | |
|---|---|---|---|
| 3,888,886 | 6/1975 | Young et al. | 260/346.75 |
| 3,907,835 | 9/1975 | Kobylinski et al. | 260/346.75 |
| 3,975,300 | 8/1976 | Burress | 252/435 |
| 3,977,998 | 8/1976 | Freerks et al. | 260/346.75 |
| 3,980,585 | 9/1976 | Kerr et al. | 252/437 |
| 3,985,775 | 10/1976 | Harrison | 260/346.75 |
| 4,002,650 | 1/1977 | Bremer et al. | 260/346.75 |
| 4,016,105 | 4/1977 | Kerr | 252/437 |
| 4,018,709 | 4/1977 | Barone et al. | 260/346.75 |
| 4,077,912 | 5/1978 | Dolhyj et al. | 252/461 |

*Primary Examiner*—Henry R. Jiles
*Assistant Examiner*—Bernard Dentz
*Attorney, Agent, or Firm*—Joseph G. Curatolo; Herbert D. Knudsen; Larry W. Evans

[57] ABSTRACT

Exceptionally reproducible catalysts comprising vanadium and phosphorus are obtained when the catalysts are prepared in an aqueous oxide slurry comprising vanadium, phosphorus and a mineral acid-free, inorganic reducing agent, which is capable of reducing the vanadium in the catalyst to a valence state below +5. Additional promoters may be selected from the group of elements of Group IB through VIB, VIII, lanthanides, actinides, and IA through VIA, excluding the elements H, N, O, C, Fr, Ra, and Po. Catalysts of particular interest consist of the elements vanadium, phosphorus, uranium and oxygen, or vanadium, phosphorus, oxygen and uranium in combination with at least one element selected from the group consisting of Ta, Ce, Cr, Mn, Co, Cu, Sb, Fe, Bi, W, Mo, Hf, Zr, Th, S, an alkali metal and an alkaline earth metal.

21 Claims, No Drawings

PRODUCTION OF MALEIC ANHYDRIDE FROM FOUR-CARBON HYDROCARBONS USING CATALYSTS PREPARED BY WATER REFLUX TECHNIQUES

BACKGROUND OF THE INVENTION

1. Field of Invention

This invention relates to a method for preparing catalysts useful in the manufacture of dicarboxylic acid anhydride by the oxidation of hydrocarbons. More particularly, it is directed to the preparation of catalysts suitable for producing maleic anhydride from n-butane, n-butenes, 1,3-butadiene or a mixture thereof.

2. Description of the Prior Art

The preparation of oxide catalysts comprising vanadium and phosphorus for use in a vapor phase oxidation of a hydrocarbon feed is known in the art. Various catalysts have been proposed wherein during the catalytic preparatory step, pentavalent vanadium in the catalyst is reduced to a valence state below +5 using a reducing agent. The conventional methods of preparing the catalysts involve combining a vanadium compound, a phosphorus compound, and when specified, promoter element compounds in an acidic reducing medium under conditions which will provide vanadium in a valence state below +5 to form a catalyst precursor, thermally convertible to an oxide or an oxide complex catalyst; recovering the catalyst precursor; and calcining the catalyst precursor at a temperature of about 350° C. to about 600° C. for at least two hours. The reducing agents employed are usually solutions of mineral acids, particularly hydrochloric acid and phosphorous acid, or organic reducing agents, especially oxalic acid. For example, U.S. Pat. No. 3,985,775 to Harrison, et al. discloses the oxidation of n-butane using a mixed vanadium-phosphorus catalyst which is prepared by dissolving vanadium pentoxide in concentrated hydrochloric acid and adding 85% phosphoric acid to the resulting solution to yield a phosphorus to vanadium ratio of 0.5:1.0 (preferably 1.2:1.0). The resulting solution is then concentrated by heating to give a 50% solid aqueous slurry and then dried to constant weight at 150° C.; the dihydrate produced is preferably in or converted into particulate form for processing through the subsequent phase transition. U.S. Pat. No. 3,975,300 to Burress, et al. teaches the use of organic reducing agents, such as glycol, sucrose, ethylene glycol, and propylene glycol, in the preparation of vanadium-phosphorus complex catalysts. U.S. Pat. No. 4,002,650 to Bremer, et al. discloses the oxidation of n-butane using a catalyst of the formula $V_{0.5-3}P_{0.5-3}U_{0.1-0.5}O_x$. The preferred preparation of the catalyst involves refluxing a mixture of vanadium pentoxide, concentrated hydrochloric acid, and uranyl acetate. To this mixture is added 85% phosphoric acid. The mixture is evaporated at atmospheric pressure, dried at 110° C. and activated by heating in an air flow at 482° C. for 16 hours. U.S. Pat. No. 3,888,886 to Young, et al. discloses the oxidation of n-butane using a vanadium-phosphorus-oxygen complex catalyst having a phosphorus:vanadium atomic ratio of 0.5:2, promoted or modified with certain transition metals, preferably zirconium, chromium, iron or hafnium. These catalysts are prepared by refluxing a reaction mixture of vanadium oxide, phosphoric acid, a hydrogen halide (usually hydrochloric acid) and a specified promoter metal compound. U.S. Pat. No. 4,018,709 discloses the vapor phase oxidation of 4-carbon n-hydrocarbons using catalysts containing vanadium, phosphorus, uranium or tungsten or a mixture of elements from zinc, chromium, uranium, tungsten, cadmium, nickel, boron and silicon. Preferably, the catalytic complex also contains an alkali metal or an alkaline earth metal, especially lithium, sodium, magnesium or barium, as active components. Catalysts are prepared in a 37% hydrochloric acid solution. U.S. Pat. No. 3,980,585 to Kerr, et al. discloses the preparation of maleic anhydride from n-4C hydrocarbons in the presence of a catalyst containing vanadium, phosphorus, copper, oxygen, tellurium or a mixture of tellurium and hafnium or uranium. The process may also be conducted in the presence of a catalyst containing vanadium, phosphorus, copper, at least one of Te, Zr, Ni, Ce, W, Pd, Ag, Mn, Cr, Zn, Mo, Re, Sm, La, Hf, Ta, Th, Co, U, Sn and optionally an element from Groups IA or IIA. This patent exemplifies the use of oxalic acid in the preparation. U.S. Pat. No. 4,016,105 teaches the preparation of a V-P complex catalyst in an aqueous phosphoric acid solution using an organic acid or aldehyde and secondary alcohol as reducing agents.

U.S. Pat. No. 3,907,835 to Kobylinski discloses the production of maleic anhydride from benzene, butene, butadiene, butanol-2 or pentanol-2 using a catalyst of the formula $U_{1-3}O_{6-16}P_{1-4}H_{0-5}$, and optionally containing vanadium. Where vanadium is present, the catalyst is prepared by mixing an anhydrous uranium salt with vanadyl oxalate (vanadium to uranium is 0.1:1 to 0.1:2) and adding enough concentrated phosphoric acid to give a uranium to phosphorus ratio of 0.2:1 to 2:1 molar ratio and phosphorus to oxygen ratio of 0.1:1 to 0.35:1 to precipitate the catalyst which is dried at 29° C. to 140° C. and heated to 425° C. to 500° C. The vanadium content of this catalyst is preferably 6 to 40 weight percent. The anhydrous uranium salt is especially a phosphate prepared by addition of a base to an aqueous solution of uranyl nitrate in concentrated phosphoric acid and drying and calcining to obtain catalytic precipitate.

Of particular interest is U.S. Pat. No. 3,977,998 to Freerks, et al., which discloses the oxidation of n-butane in the presence of a phosphorus-vanadium-oxygen complex catalyst, wherein the phosphorus to vanadium atom ratio is 1–2:2–1, the catalyst being prepared by (a) contacting a vanadium compound and a phosphorus compound in acid solution containing a reducing agent under conditions which will provide at least 50 1 atom percent of vanadium in tetravalent form; (b) separating the prepared catalyst precursor, and (c) calcining the catalyst precursor at 350° C. 660° C. for at least two hours, the improvement comprising that the calcination is effected in an inert atmosphere. The reducing agent may be a hydrogen halide acid or oxalic acid, but is preferably a mixture of phosphoric acid containing sufficient phosphorous acid to reduce $V^{+5}$. Preferred catalyst precursors have a phosphorus to vanadium atom ratio of 1:1 to 1.5:1, especially 1:1 to 1.2:1. Exemplified in this patent is the use of a catalyst of the formula $P_{1.05}V_1O_x$ prepared by digesting vanadium pentoxide in a mixture of water, 85% phosphoric acid and 99.4% phosphorous acid. This mixture was heated to 100° C. in an autoclave which was then sealed; the mixture was heated for 3 hours at 145° C. and a solid catalyst precursor was collected and slurried in 20 weight percent water. Viscous putty was extruded through a 0.35 cm. diameter die and cut into pellets, then air-dried and heated to 125° C. Pellets were heated in a muffle furnace to 350° C. for one hour and then to 375° C. an additional hour. The air in the furnace was replaced by nitrogen gas, and the temperature was raised to 500° C. over a five hour period. The catalyst was cooled rapidly to room temperature under nitrogen gas and possessed a 93 atom percent of vanadium as $V^{+4}$.

U.S. Pat. No. 4,077,912 to Dolhyj, et al. discloses that strongly exothermic reactions are controlled by the use of a catalyst which comprises (a) an inert support of at least about 20 microns in diameter, said support having an outer surface, and (b) a coating of a catalytically active material on the outside surface of the support which strongly adheres to the outer surface of the support. The Dolhyj, et al. patent broadly discloses that preferred catalysts contain the active catalytic component oxides of alkali metals, alkaline earth metals, vanadium, chromium, molybdenum, tungsten, manganese, iron, cobalt, nickel, copper, zinc, indium, thallium, tin, antimony, bismuth, phosphorus and arsenic. Especially preferred among these catalysts are those which contain at least the oxides of antimony and molybdenum. Specifically, the patent in claim 5 delineates the catalytically active oxide material and especially refers to the optional use of phosphorus as a catalytic constituent. By sharp contrast, the base catalyst employed in the present invention requires the presence of phosphorus as an integral catalytic constituent. Whereas phosphorus is a highly desirable active catalytic constituent of the catalysts employed in the present invention, the same is not shown as being effective as an ingredient in the catalysts containing vanadium which are utilized in the preparation of maleic anhydride at columns 4 and 5.

All of these teachings in the prior art have failed to achieve the desirable results obtained by the use of the present invention. The activity and quality of catalysts prepared using conventional prior art techniques are diverse because catalysts containing vanadium and phosphorus are especially sensitive to their mode of preparation. Using the present invention, reproducible catalysts of enhanced activity and selectivity are obtained.

SUMMARY OF THE INVENTION

It is an object of the present invention to provide an improved process for the vapor phase oxidation of n-butane, n-butenes, 1,3-butadiene or a mixture thereof to maleic anhydride.

It is a further object of this invention to provide a method for preparing an oxide catalyst comprising vanadium, phosphorus, uranium and oxygen.

In accordance with the present invention has been discovered a process for the preparation of maleic anhydride by the oxidation of n-butane, n-butenes, 1,3-butadiene, or a mixture thereof with molecular oxygen in the vapor phase at a reaction temperature of 250° C. to 600° C. in the presence of a catalyst comprising the mixed oxides of vanadium and phosphorus, the improvement wherein the catalyst is prepared by:

(a) forming an aqueous oxide slurry of a vanadium compound containing pentavalent vanadium;

(b) adding to said aqueous oxide slurry a reducing agent capable of reducing said pentavalent vanadium to a valence state below +5 to obtain an aqueous slurry containing reduced vanadium, wherein said reducing agent is selected from the group consisting of ammonia, hydrazine, hydrazine hydrate, a finely divided metal or colloidal metal;

(c) adding a compound containing uranium immediately before the addition of the reducing agent or after the addition of the reducing agent;

(d) adding a phosphorus compound containing pentavalent phosphorus before the addition of the reducing agent or after the addition of the reducing agent;

(e) removing the water from the resulting slurry to form a dried catalyst; and (f) calcining the dried catalyst at a temperature of 250° C. to 600° C.

Effective results are observed when the catalyst is based solely upon vanadium, phosphorus, uranium and oxygen but, from the standpoint of optimum benefits and catalyst effectiveness, additional promoters may be selected from the group consisting of elements of Groups IB through VIB, VIII, lanthanides, actinides, and Groups IA through VIA, excluding the elements H, N, O, C, Fr, Ra, and Po. Catalysts of particular interest consist of the elements vanadium, phosphorus, uranium, oxygen and optionally at least one of Ta, Ce, Cr, S, Mn, Co, Cu, Sb, Fe, Bi, W, Hf, Zr, Th, an alkaline earth metal and an alkali metal. Of these promoter elements, Ta, Ce, Mn, Co, Sb, Fe, Bi and W are preferred.

Although preferably the compound containing pentavalent vanadium is reacted with the compound containing uranium prior to the addition of the reducing agent and a compound containing pentavalent phosphorus is subsequently added to the resulting slurry, beneficial results are achieved by reacting the compound containing pentavalent vanadium with compounds containing pentavalent phosphorus and uranium, respectively, followed by reaction with the reducing agent, or by reacting the four components together followed by the addition of compounds containing the respective promoter elements. However, superior results are observed when the compounds containing the respective promoter elements are added to the aqueous slurry containing reduced vanadium immediately preceeding the addition of the compound containing pentavalent phosphorus.

Ultimate results are achieved using an oxide catalyst comprising:

$$V_aP_bU_cO_x$$

wherein
a and b are 0.1 to 10;
c is 0.01 to 5;
x is the number of oxygens required to satisfy the valence requirements of the other elements present; and wherein
said catalyst optionally contains at least one element selected from the group consisting of tantalum, cerium, chromium, manganese, sulfur, cobalt, copper, antimony, iron, bismuth, tungsten, molybdenum, alkaline earth metal, an alkali metal, hafnium, zirconium, and thorium.

An optional promoter may be present in the catalyst in an atomic range of 0.01 to 5, preferably 0.01 to 1. Especially desirable results are obtained using catalysts wherein a and b are 0.5 to 3, catalysts wherein c is 0.1 to 0.5, and catalysts wherein a divided metal or colloidal metal is present in the catalyst in an atomic range of 0.01 to 5.

The method employed in preparing the catalyst is critical to the process for producing maleic anhydride. Maximum conversions of maleic anhydride are obtained where the starting material is n-butane or n-butenes. Essentially all the product produced in this process is maleic anhydride with only minor amounts of lower acids being detected.

The method employed in preparing the catalyst departs from the classical procedures involving reducing the vanadium in the catalyst to a valence state below +5 using an acid, such as a hydrogen halide acid or an organic acid, in particular hydrochloric acid or oxalic acid, as the reducing agent. By the preferred procedure of the invention a compound containing pentavalent vanadium in an aqueous suspension or slurry is pre-reduced in a controlled manner so that at least some of the vanadium is reduced to a valence state below +5 before the compound containing pentavalent vanadium is mixed with a compound containing pentavalent phosphorus, followed by drying the aqueous mixture and calcining the resulting product.

The method employed preferably comprises the simple mixing of the respective metal oxides of a compound containing pentavalent vanadium, a compound containing uranium, and a reducing agent. The mixing of the components may be carried out mechanically in a blender or in a ball mill, or the respective oxides may be mixed as a slurry in water. Advantageously, the phosphorus compound is added at this juncture. This initial step is followed by calcination at a moderate temperature, generally not above 600° C. It is hypothesized that the color which developes in the catalyst is the result of the reduction of vanadium, at least in part, to a lower oxidation state in the oxidation-reduction reaction occurring between pentavalent vanadium and the reducing agent.

Suitable vanadium compounds containing pentavalent vanadium include: vanadium pentoxide or vanadium salts, such as ammonium metavanadate, and vanadium oxytrihalides, however, vanadium pentoxide is preferred. Suitable phosphorus compounds containing pentavalent phosphorus include: phosphoric acid, phosphorus pentoxide, or phosphorus perhalides, such as phosphorus pentachloride, however, phosphoric acid and phosphorus pentoxide are preferred.

Representative examples of suitable reducing agents include hydrazine, hydrazine hydrate, ammonia, or finely divided or colloidal metals of molybdenum, tungsten, magnesium, aluminum, or nickel. When powdered metals are employed, the amount of metal reacted ranges from 0.01 to 5 gram-atoms per mole of the pentavalent vanadium present. It is to be understood that in accordance with the present invention suitable reducing agents do not include inorganic acids, such as phosphorous acid and hydrogen halide acids, or organic reducing agents, such as oxalic acid, citric acid, formic acid, ascorbic acid, malic acid, glycol, sucrose, ethylene glycol, and propylene glycol, aldehydes, such as formaldehyde and acetaldehyde, or an alcohol.

An especially preferred procedure of the invention involves refluxing an aqueous slurry of a vanadium compound containing pentavalent vanadium, a reducing agent, and at least one compound containing the respective promoter elements for a period of ½ hour to 16 hours, and preferably from about 1 to 4 hours. Following this the pentavalent phosphorus compound is added and the slurry is heated from ½ hour to 16 hours, and preferably from about 1 to 4 hours. The amount of water present in the solution can range from 500 to 2000 mls. per gram-atom of vanadium present. During the initial period the slurry darkens in color. Water is removed from the slurry by evaporation until a thick homogeneous material is obtained when on drying at 110° C. overnight emerges as a solid.

A reproducible method of combining the catalytic ingredients comprises:

(a) refluxing an aqueous oxide slurry containing vanadium pentoxide;

(b) adding to said aqueous oxide slurry a mineral acid-free, inorganic reducing agent capable of reducing the vanadium in the vanadium pentoxide to a valence state below +5 to obtain an aqueous slurry containing reduced vanadium;

(c) adding a uranium compound immediately before the addition of the reducing agent or after the addition of the reducing agent;

(d) adding phosphoric acid before the addition of the reducing agent or after the addition of the reducing agent;

(e) removing the water from the resulting slurry to form a dried catalyst; and (f) calcining the dried catalyst a temperature of 250° C. to 600° C.

Excellent results are obtained using a coated catalyst consisting essentially of an inert support material having a diameter of at least 20 microns and an outer surface, and a continuous coating of said active catalyst on said inert support strongly adhering to the outer surface of said support. The special coated catalyst consists of an inert support material having an outer surface and a coating of the active catalytic material on this outer surface.

The support material for the catalyst forms the inner core of the catalyst. This is an essentially inert support and may have substantially any particle size although a diameter of at least 20 microns is preferred. Especially preferred in the present invention for use in a commercial reactor are those supports which are spherical and which have a diameter of about 0.2 cms. to about 2 cms. Suitable examples of essentially inert support materials include: Alundum®, silica, alumina, alumina-silica, silicon carbide, titania and zirconia. Especially preferred among these supports are Alundum®, silica, alumina and alumina-silica.

The catalysts may contain essentially any proportions of the support and catalytically active material. The limits of this relationship are only set by the relative ability of the catalyst and support material to accommodate each other. Preferred catalysts contain about 10% to about 100% by weight of catalytically active material based on the weight of the support.

The preparation of these coated catalysts can be accomplished by various techniques. The basic method of preparing these catalysts is to partially wet the support material with a liquid. The support cannot be wet on the outer surface of the total mass. It should be dry to the touch. If the support is wet, then the active catalytic material will agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum and adding the active catalytic material until none is taken up by the support. This is very economically done.

The catalyst is activated by calcining it in air or an oxygen-containing gas at a temperature of 250° C. to 600° C. for a period of up to 5 hours or more. A preferred activation of the catalyst is accomplished by passing a mixture of steam and air or air alone over the catalyst at a temperature of about 300° C. to 500° C. for a period of about 1 to 5 hours. The hydrocarbon reacted may be n-butane, n-butenes, 1,3-butadiene or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, Alundum ®, silicon carbide, boron phosphate, zirconia, titania, and the like. The catalysts are conveniently used in a fixed-bed reactor using tablets, pellets or the like, or in a fluid-bed reactor using a catalyst preferably having a particle size of less than about 300 microns. The contact time may be as low as a fraction of a second or as high as 50 seconds. The reaction may be conducted at atmospheric, superatmospheric or subatmospheric pressure.

SPECIFIC EMBODIMENTS

Examples 1 to 33 and Comparative Examples 1 to 24

Example 1

A catalyst of the formula $V_{1.0}P_{1.15}U_{0.20}O_x+W°_{0.166}$ was prepared as follows:

Part A: 36.37 grams of $V_2O_5$ and 22.4 grams of $U_3O_8$ were ball milled with 250 mls. of distilled water for 3 hours and the resulting mixture was allowed to stand overnight. The next morning the mixture was ball milled an additional 2 hours. Said mixture, having a 600 ml. volume, was rinsed into a 2-liter beaker. 12.26 grams of tungsten metal powder were added and the resulting mixture was stirred and refluxed. When boiling commenced the color of the resulting mixture changed from yellow-brown to dark green. Said mixture was refluxed for 2¼ hours and became black in appearance. 53.0 grams of 85% phosphoric acid were added and the color of the mixture changed to dark green. The resulting mixture was refluxed for 1 hour, evaporated to a thick paste, dried overnight in an oven at 110° C., and calcined for 2 hours at 482° C. The resulting catalyst, hard and dark green in appearance, was ground to 10/30 mesh size.

Part B: 36.37 grams of $V_2O_5$ and 22.4 grams of $U_3O_8$ were ball milled with 250 mls. of distilled water for 5 hours. Said mixture, having a 600 ml. volume, was rinsed into a 2-liter beaker. 12.26 grams of tungsten metal powder were added and the resulting mixture was refluxed for 2 hours. The color of the resulting mixture changed to green then to black; said mixture was allowed to stand overnight. The next morning the mixture was heated to reflux, boiled for 15 minutes, and then 53.0 grams of 85% phosphoric acid were added. The mixture was refluxed for 1 hour and became dark green in appearance. The mixture was allowed to evaporate to a thick black shiny paste, dried overnight at 110° C. to 130° C. and calcined in an oven for 2 hours at 482° C. The resulting catalyst resembled the catalyst prepared in Part A.

Part C: 36.37 grams of $V_2O_5$ and 22.40 grams of $U_3O_8$ were ball milled overnight in about 800 mls. of distilled water in a 2-liter beaker. To this slurry were added 12.26 grams of powdered tungsten metal and the resulting slurry was refluxed on a hotplate at 71° C. for about 2.5 hours. 53.0 grams of 85% $H_3PO_4$ were slowly added and the color changed from blackish-green to medium green. The temperaure was maintained at 65.6° C. for 1 hour and evaporation commenced at about 57.2° C. with nitrogen blowing. Evaporation was continued for 2 days. The temperature was increased to 76.7° C. and the material was evaporated to dryness, dried in an oven at 110° C., and calcined for 2 hours at 428° C. The final product was hard, porous and green in appearance.

Example 2

A catalyst of the formula $V_{1.0}P_{1.15}U_{0.20}O_x$ (hydrazine hydrate employed as the reducing agent) was prepared as follows:

Part A: 33.6 grams of $V_2O_5$ were suspended in 450 mls. of distilled water in a 2-liter beaker and stirred with a magnetic bar stirrer. To this suspension were added 4.7 grams of 99% to 100% hydrazine hydrate, the color immediately darkened to deep blackish-brown. The resulting solution was allowed to reflux for about 1 hour and then 31.34 grams of uranyl acetate dihydrate were added and refluxing was continued for about 1 additional hour. To this solution were added 48.96 grams of 85% $H_3PO_4$; the color of the solution very shortly changed to green and refluxing was continued for 2 hours. This mixture was allowed to stand overnight and the next morning a green precipitate with a dark blue supernatant layer had formed. The material was redispersed with the stirrer bar and allowed to evaporate to a thick paste, dried overnight at 100° C., calcined for 3½ hours at 260° C., and ground and screened to 10/30 mesh size.

Part B: 33.6 grams of $V_2O_5$ were suspended in 450 mls. of distilled water in a 2-liter beaker and stirred with a magnetic bar stirrer. To this suspension were added dropwise 5.53 grams of 99% to 100% hydrazine hydrate; the color of the suspension changed to dark green. The resulting solution was refluxed for 1 hour; the color changed to black, 31.34 grams of uranyl acetate were added; there was no apparent change in color and refluxing continued for an additional hour. 48.96 grams of 85% $H_3PO_4$ were added to the black slurry and allowed to reflux for an additional 2 hours. After the addition of $H_3PO_4$ the color changed in about 10 minutes to a deep dark green and remained green during the reflux period. The slurry evaporated to a thick black-green paste, dried at about 120° C., and calcined for 2 hours at 482° C.

Part C: The preparation was the same as in Part B except after the addition of $H_3PO_4$ and ½ hour of reflux, the supernatant liquid was black-blue and a thick, sticky carbon monoxide, carbon dioxide and oxygen were determined using a Carle A.G.C. 111 equipped with a heated column oven, wherein the column system consisted of molecular sieves and sebacyl chloride on chromosorb. The reaction conditions and results of the experiments are shown in Tables I and II. The following definitions are used in measuring the carbon atoms in the feed and the product.

% Single Pass Yield To Total Acid =
$$\frac{\text{moles carbon as total acid}}{\text{moles carbon as hydrocarbon fed}} \times 100$$

% Selectivity To Total Acid =
$$\frac{\text{moles carbon as total acid}}{\text{moles carbon fed as hydrocarbon} - \text{moles carbon as hydrocarbon recovered}} \times 100$$

Use of the catalysts prepared above is summarized as follows:

| Catalyst Preparation | Use of Catalyst Prepared | |
|---|---|---|
| | Table | Experiment No. |
| 1A | I | 3 to 13 |
| | II | 26 and 27 |
| 1B | I | 14 to 19 |
| 2A | I | 20 and 21 |
| | II | 28 to 30 |
| 2B | II | 31 |
| 2C | II | 32 |
| 2D | I | 22 |
| 2E | I | 23 to 25 |
| Comparative 1A | I | Comp. 4 to 7 |
| | II | Comp. 23 to 25 |
| Comparative 1B | I | Comp. 8 to 13 |
| Comparative 1C | I | Comp. 14 to 20 |
| | II | Comp. 26 and 27 |
| Comparative 2 | I | Comp. 21 |
| Comparative 3 | I | Comp. 22 |

TABLE I

Reaction of n-Butane Using Catalysts Prepared by Invention Compared with Catalysts Prepared by Prior Art Methods

| Example | Catalyst | Temp. °C. Bath | Temp. °C. Reactor | Results, % Single Pass Yield Total Acid* | Selectivity, Total Acid | Hours On Stream | Air/n-Butane Ratio |
|---|---|---|---|---|---|---|---|
| 3 | $V_{1.0}P_{1.15}U_{0.20}O_x + W°_{0.166}$ | 482.22 | 493.33 | 41.00 | 46.4 | 2.7 | 62.0 |
| 4 | $V_{1.0}P_{1.15}U_{0.20}O_x + W°_{0.166}$ | 485.00 | 512.78 | 33.20 | 33.2 | 241.0 | 61.5 |
| 5 | $V_{1.0}P_{1.15}U_{0.20}O_x + W°_{0.166}$ | 465.56 | 487.78 | 38.10 | 38.1 | 263.0 | 60.0 |
| 6 | $V_{1.0}P_{1.15}U_{0.20}O_x + W°_{0.166}$ | 454.44 | 472.22 | 42.70 | 42.7 | 267.0 | 62.0 |
| 7 | $V_{1.0}P_{1.15}U_{0.20}O_x + W°_{0.166}$ | 454.44 | 471.11 | 42.30 | 42.3 | 286.0 | 62.0 |
| 8 | $V_{1.0}P_{1.15}U_{0.20}O_x + W°_{0.166}$ | 440.56 | 450.00 | 44.10 | 47.0 | 290.0 | 61.0 |
| 9 | $V_{1.0}P_{1.15}U_{0.20}O_x + W°_{0.166}$ | 443.33 | 454.44 | 46.50 | 49.1 | 313.0 | 65.0 |
| 10 | $V_{1.0}P_{1.15}U_{0.20}O_x + W°_{0.166}$ | 446.11 | 454.44 | 42.60 | 46.1 | 334.0 | 88.0 |
| 11 | $V_{1.0}P_{1.15}U_{0.20}O_x + W°_{0.166}$ | 446.11 | 455.56 | 46.70 | 46.6 | 339.0 | 82.0 |
| 12 | $V_{1.0}P_{1.15}U_{0.20}O_x + W°_{0.166}$ | 444.44 | 455.56 | 48.60 | 48.6 | 461.0 | 67.5 |
| 13 | $V_{1.0}P_{1.15}U_{0.20}O_x + W°_{0.166}$ | 446.11 | 460.00 | 47.70 | 47.7 | 558.0 | 64.0 |
| 14 | $V_{1.0}P_{1.0}U_{0.20}O_x + W°_{0.166}$ (duplicate I) | 485.00 | 504.44 | 31.60 | 32.5 | 1.6 | 93.0 |
| 15 | $V_{1.0}P_{1.0}U_{0.20}O_x + W°_{0.166}$ (duplicate I) | 456.11 | 472.78 | 43.90 | 46.4 | 3.2 | 93.0 |
| 16 | $V_{1.0}P_{1.15}U_{0.20}O_x + W°_{0.166}$ (duplicate I) | 457.22 | 475.00 | 44.90 | 46.4 | 27.4 | 94.0 |
| 17 | $V_{1.0}P_{1.15}U_{0.20}O_x + W°_{0.166}$ (duplicate I) | 457.22 | 479.44 | 39.00 | 41.0 | 97.3 | 96.0 |
| 18 | $V_{1.0}P_{1.15}U_{0.20}O_x + W°_{0.166}$ (duplicate I) | 441.11 | 462.78 | 48.60 | 49.3 | 143.0 | 99.0 |
| 19 | $V_{1.0}P_{1.15}U_{0.20}O_x + W°_{0.166}$ (duplicate I) | 450.56 | 469.44 | 44.10 | 44.1 | 71.9 | 93.0 |
| 20 | $V_{1.0}P_{1.15}U_{0.20}O_x$ (reduced with hydrazine hydrate) | 496.00 | 512.00 | 32.60 | 33.4 | 1.6 | 67.0 |
| 21 | $V_{1.0}P_{1.15}U_{0.20}O_x$ (reduced with hydrazine hydrate) | 481.00 | 499.00 | 33.40 | 34.9 | 25.3 | 89.0 |
| 22 | $V_{1.0}P_{1.15}U_{0.20}O_x$—Duplicate III (reduced with hydrazine hydrate) | 510.00 | 514.00 | 20.60 | 32.0 | 2.3 | 119.0 |
| 23 | $V_{1.0}P_{1.15}U_{0.20}O_x$—Duplicate IV (reduced with hydrazine hydrate) | 482.00 | 486.00 | 27.30 | 48.0 | 0.8 | 84.5 |
| 24 | $V_{1.0}P_{1.15}U_{0.20}O_x$—Duplicate IV (reduced with hydrazine hydrate) | 496.00 | 504.00 | 31.30 | 47.0 | 3.5 | 90.0 |
| 25 | $V_{1.0}P_{1.15}U_{0.20}O_x$—Duplicate IV (reduced with hydrazine hydrate) | 537.00 | 549.00 | 32.50 | 36.0 | 4.6 | 90.0 |
| Comp. 4 | $V_{1.0}P_{1.15}U_{0.20}O_x$ (prepared using HCl) | 484.00 | 500.00 | 41.20 | 44.6 | 8.0 | 97.0 |
| Comp. 5 | $V_{1.0}P_{1.15}U_{0.20}O_x$ (prepared using HCl) | 484.00 | 500.00 | 41.20 | 44.1 | 107.0 | 91.0 |
| Comp. 6 | $V_{1.0}P_{1.15}U_{0.20}O_x$ (prepared using HCl) | 484.00 | 506.00 | 39.90 | 42.9 | 126.0 | 61.0 |
| Comp. 7 | $V_{1.0}P_{1.15}U_{0.20}O_x$ (prepared using HCl) | 485.00 | 501.00 | 41.70 | 43.3 | 201.0 | 84.0 |
| Comp. 8 | $V_{1.0}P_{1.15}U_{0.20}O_x$ (HCl duplicate I) | 490.60 | 510.00 | 40.20 | 43.3 | 4.9 | 76.0 |
| Comp. 9 | $V_{1.0}P_{1.15}U_{0.20}O_x$ (HCl duplicate I) | 487.80 | 507.20 | 34.00 | 36.0 | 94.7 | 75.0 |
| Comp. 10 | $V_{1.0}P_{1.15}U_{0.20}O_x$ (HCl | 456.10 | 468.30 | 37.90 | 50.3 | 99.0 | 76.0 | precipitate formed. The material was refluxed for 2 hours, evaporated to a thick paste, dried at about 120° C., and calcined for 2 hours at 482° C. producing a material having the same appearance as that in Part B.

Part D: 36.37 grams of $V_2O_5$ were dispersed in 450 mls. of distilled water in a 2-liter beaker equipped with a magnetic bar stirrer. To this solution were added 3.3 grams of 99% to 100% hydrazine hydrate. This mixture was refluxed for about an hour and allowed to stand at rest overnight. The next morning the mixture was heated to reflux and 22.45 grams of $U_3O_8$ were added. The resulting mixture was refluxed for one hour and 53.0 grams of 85% $H_3PO_4$ were then added. Refluxing was resumed for an additional 2 hours and the mixture was evaporated to dryness, dried overnight in an oven at 110° C. and calcined for 3 hours at 260° C. The resulting catalyst, hard and green in appearance, was ground and screened to 10/30 mesh size.

Part E: 36.37 grams of $V_2O_5$ were dispersed in 450 mls. of distilled water in a 2-liter beaker equipped with a magnetic bar stirrer. To this solution were added 53.0 grams of 85% $H_3PO_4$, followed by the addition of 5.07 grams of 99% to 100% hydrazine hydrate. The resulting mixture was heated and refluxed for about one hour. The resulting mixture, deep blue-green in appearance, was allowed to stand at rest overnight; the next morning the mixture was refluxed and 22.45 grams of $U_3O_8$ were added. Refluxing was resumed an additional 2 hours; the color of the mixture changed to black. The resulting mixture was evaporated to dryness, dried over the weekend in an oven at 110° C., and calcined for 3 hours at 260° C.

COMPARATIVE EXAMPLES 1 TO 3

Catalysts were prepared using (1) hydrochloric acid as a reducing agent, or (2) oxalic acid as a reducing agent.

Comparative Example 1

$V_{1.0}P_{1.15}U_{0.20}O_x$ (Vanadium reduced with hydrochloric acid)

Part A: 33.0 grams of vanadium pentoxide were digested in 440 mls. of concentrated hydrochloric acid and refluxed with stirring for 1.5 hours. Color gradually changed from brown to blue. To this reflux slurry were added 31.0 grams of uranyl acetate dihydrate and the resulting mixture was refluxed an additional hour. 49.0 grams of 85% phosphoric acid were added and the mixture was refluxed 2.0 hours. The total mixture was evaporated over a 3.5 hour period and dried in an oven at 110° C. overnight. The catalyst was ground and screened to give a 10×30 mesh fraction and was activated by calcining in an air flow at 260° C. for 3 hours. The final product was hard, and dark green in appearance.

Part B: A duplicate catalyst was prepared in the same manner described in Part A, except after vanadium pentoxide was digested in hydrochloric acid, the mixture was refluxed for 2.0 hours; total mixture was evaporated over a 1.5 hour period; dried in an oven an additional 4 hours at 125° C.; and calcined in air at 288° C. for 3 hours. The final product was green with gold flaws in appearance Part C: A second duplicate catalyst was prepared in the same manner described in Part A.

Comparative Example 2

$V_{1.0}P_{3.2}U_{0.20}O_x$ (Vanadium reduced with oxalic acid)

This catalyst was prepared as follows: 36.37 grams of vanadium pentoxide were dispersed in 200 mls. of distilled water and stirred with a magnetic bar at 80° C. To this aqueous solution, 95 grams of oxalic acid were slowly added. Gas evolved and the solution gradually darkened to deep blue. 33.93 grams of uranyl acetate dihydrate were added and the resulting mixture was refluxed for ½ hour, then 47.58 grams of 85% phosphoric acid were added. Refluxing continued for 2 hours. The mixture was permitted to cool to room temperature overnight. Liquors were removed, and the remainder was evaporated to a thick paste, dried in an oven for 4 days, and calcined at 288° C. in air for 3 hours. Final product was "blown" and light blue-green in appearance.

Comparative Example 3

A catalyst of the formula $V_{1.0}P_{1.0}U_{0.20}O_x$ was prepared by preforming a $V_2O_5$—$P_2O_5$ complex, then reducing $V^{+5}$ as follows: A first solution was prepared consisting of 11.6 grams of $NH_4VO_3$ and 600 mls. of distilled water. A second solution was prepared consisting of 23 grams of $NH_4H_2PO_4$ and 150 mls. of distilled water. The second solution was added to the first, and the color of the first solution changed from yellow to deep orange. To this mixture, concentrated nitric acid was added dropwise until the mixture was red in appearance. The mixture was refluxed and 31.0 grams of uranyl acetate dihydrate were added resulting in a deep orange gellation. The mixture was allowed to stand overnight and the next day enough distilled water was added to bring the volume up to 500 mls. Hydrazine hydrate was added dropwise until the color of the slurry changed from red to green to gray. The resulting mixture was refluxed for 5 hours, boiled to dryness, dried in an oven overnight at 105° C., and calcined for 2 hours in air at 488° C. The final product was light, fluffy, and blue-green-gray in appearance.

EXAMPLES 3 TO 32 AND COMPARATIVE EXAMPLES 4 TO 27

Preparation of Maleic Anhydride Using Catalysts Prepared By the Invention Compared with Performance of Catalysts Prepared by Prior Art Techniques A 20 cc. fixed-bed reactor was constructed equipped with a split-feed induction system. Catalysts prepared as described below were charged to the reactor and heated to the reaction temperature and n-butane or 2-butene was reacted with air in the proportions specified in Tables I and II at an apparent contact time of 1 to 2 seconds. N-butane or 2-butene was premixed with a small portion of a total quantity of air in a 30 cm. packed tube as the mixture was regulated to a splitter allowing only a slip stream to flow to the reactor. The remainder of air was added just prior to the inlet of the reactor. Liquid product was recovered in aqueous scrubbers and titrated for total acid. When n-butane was repeated, product samples were found to be 98% pure maleic anhydride; and when 2-butene was reacted, product samples were found to be 80% to 90% maleic anhydride. Off-gas analyses for 4-carbon hydrocarbons,

TABLE I-continued

Reaction of n-Butane Using Catalysts Prepared by Invention Compared with Catalysts Prepared by Prior Art Methods

| Example | Catalyst | Temp. °C. Bath | Temp. °C. Reactor | Results, % Single Pass Yield Total Acid* | Selectivity, Total Acid | Hours On Stream | Air/n-Butane Ratio |
|---|---|---|---|---|---|---|---|
| Comp. 11 | $V_{1.0}P_{1.15}U_{0.20}O_x$ (HCl duplicate I) | 483.90 | 501.70 | 38.90 | 42.0 | 101.0 | 74.0 |
| Comp. 12 | $V_{1.0}P_{1.15}U_{0.20}O_x$ (HCl duplicate I) | 429.40 | 451.70 | 11.50 | 50.0 | 120.0 | 74.0 |
| Comp. 13 | $V_{1.0}P_{1.15}U_{0.20}O_x$ (HCl duplicate I) | 445.00 | 465.60 | 27.80 | 52.0 | 123.0 | 26.0 |
| Comp. 14 | $V_{1.0}P_{1.15}U_{0.20}O_x$ (HCl duplicate II) | 480.00 | 490.00 | 53.90 | 53.9 | 2.0 | 113.0 |
| Comp. 15 | $V_{1.0}P_{1.15}U_{0.20}O_x$ (HCl duplicate II) | 484.00 | 501.00 | 48.70 | 50.0 | 20.5 | 87.0 |
| Comp. 16 | $V_{1.0}P_{1.15}U_{0.20}O_x$ (HCl duplicate II) | 482.00 | 504.00 | 37.40 | 39.2 | 93.3 | 88.0 |
| Comp. 17 | $V_{1.0}P_{1.15}U_{0.20}O_x$ (HCl duplicate II) | 485.00 | 497.00 | 54.90 | 60.0 | 99.0 | 45.0 |
| Comp. 18 | $V_{1.0}P_{1.15}U_{0.20}O_x$ (HCl duplicate II) | 484.00 | 495.00 | 51.20 | 58.7 | 102.0 | 44.0 |
| Comp. 19 | $V_{1.0}P_{1.15}U_{0.20}O_x$ (HCl duplicate II) | 491.00 | 505.00 | 48.90 | 53.3 | 105.0 | 45.0 |
| Comp. 20 | $V_{1.0}P_{1.15}U_{0.20}O_x$ (HCl duplicate II) | 489.00 | 504.00 | 39.50 | 44.9 | 108.0 | 44.0 |
| Comp. 21 | $V_{1.0}P_{1.15}U_{0.20}O_x$ (prepared using oxalic acid) | 537.00 | 537.00 | 1.30 | 11.0 | 1.2 | 92.0 |
| Comp. 22 | $V_{1.0}P_{1.0}U_{0.20}O_x + W°_{0.166}$ (V-P preformed with nitric acid) | 518.30 | 522.80 | 10.20 | 15.4 | 19.0 | 94.0 |

*at least 98% maleic anhydride.

TABLE II

Oxidation of 2-Butene Using Catalysts Prepared by Invention Compared with Catalysts Prepared by Prior Art Methods

| Example | Catalyst | Temp. °C. Bath | Temp. °C. Reactor | Results, % Single Pass Yield Total Acid* | Maleic Anhydride | Selectivity, Total Acid | Hours On Stream | Air/2-Butene Ratio |
|---|---|---|---|---|---|---|---|---|
| 26 | $V_{1.0}P_{1.15}U_{0.20}O_x + W°_{0.166}$ | 405.56 | 434.44 | 34.80 | | 50.1 | 466.0 | 59.0 |
| 27 | $V_{1.0}P_{1.15}U_{0.20}O_x + W°_{0.166}$ | 402.22 | 437.78 | 33.50 | | 33.5 | 534.0 | 75.0 |
| 28 | $V_{1.0}P_{1.15}U_{0.20}O_x$ (reduced with hydrazine hydrate) | 426.67 | 442.22 | 51.40 | 46.1 | 51.4 | 1.4 | 74.5 |
| 29 | $V_{1.0}P_{1.15}U_{0.20}O_x$ (reduced with hydrazine hydrate) | 412.78 | 426.67 | 55.30 | 48.8 | 58.7 | 5.0 | 74.9 |
| 30 | $V_{1.0}P_{1.15}U_{0.20}O_x$ (reduced with hydrazine hydrate) | 412.78 | Undetermined | 57.30 | 51.3 | 57.3 | 26.5 | 80.3 |
| 31 | $V_{1.0}P_{1.15}U_{0.20}O_x$ (duplicate I) | 750° F. | 788.00 | 64.80 | | | 22.3 | 49.70 |
| 32 | $V_{1.0}P_{1.15}U_{0.20}O_x + W°_{0.166}$ (duplicate II) | 750° F. | 875.00 | 69.75 | | | 48.8 | 50.72 |
| Comp 23 | $V_{1.0}P_{1.15}U_{0.20}O_x$ (HCl digestion) | 426.00 | 483.00 | 53.40 | 47.4 | 53.4 | 26.6 | 46.7+18.8$H_2O$ |
| Comp 24 | $V_{1.0}P_{1.15}U_{0.20}O_x$ (HCl digestion) | 421.00 | 479.00 | 55.90 | 48.3 | 55.9 | 29.0 | 47.2+19.1$H_2O$ |
| Comp 25 | $V_{1.0}P_{1.15}U_{0.20}O_x$ (HCl digestion) | 421.00 | 502.00 | 44.70 | | | 96.7 | 68.5 |
| Comp 26 | $V_{1.0}P_{1.15}U_{0.20}O_x$ (duplicate II) | 385.00 | 413.00 | 55.30 | 42.6 | 56.6 | 3.2 | 68.1 |
| Comp 27 | $V_{1.0}P_{1.15}U_{0.20}O_x$ (duplicate II) | 385.00 | 413.00 | 55.30 | Duplicate of preceeding run | 42.6 | 3.2 | 68.1 |

*measured as total acid, of which 80% to 90% is maleic anhydride

We claim:

1. In a process for the production of maleic anhydride by the oxidation of n-butane, n-butenes, 1,3-butadiene or a mixture thereof with molecular oxygen in the vapor phase at a reaction temperature of 250° C. to 600° C. in the presence of a catalyst comprising the mixed oxides of vanadium, phosphorus and uranium, the improvement wherein the catalyst is prepared by (a) forming an aqueous oxide slurry of a vanadium compound containing pentavalent vanadium;
(b) adding to said aqueous oxide slurry a mineral acid-free, inorganic reducing agent capable of reducing said pentavalent vanadium to a valence state below +5 to obtain an aqueous slurry containing reduced vanadium, wherein said reducing agent is selected from the group consisting of ammonia, hydrazine, hydrazine hydrate, a finely divided metal or colloidal metal;
(c) adding a compound containing uranium immediately before the addition of the reducing agent or after the addition of the reducing agent;
(d) adding a phosphorus compound containing pentavalent phosphorus before the addition of the reducing agent or after the addition of the reducing agent;
(e) heating said aqueous oxide slurry under reflux conditions;
(f) removing the water from the resulting slurry to form a dried catalyst; and
(g) calcining the dried catalyst at a temperature of 250° C. to 600° C.

2. The process of claim 1 wherein n-butane is reacted.

3. The process of claim 1 wherein an n-butene is reacted.

4. The process of claim 1 wherein the catalyst comprises

$$V_a P_b U_c O_x$$

wherein
a and b are 0.1 to 10;
c is 0.01 to 5;
x is the number of oxygens required to satisfy the valence requirements of the other elements present; and
wherein
said catalyst optionally contains at least one element selected from the group consisting of tantalum, cerium, chromium, manganese, sulfur, cobalt, copper, antimony, iron, bismuth, tungsten, molybdenum, alkaline earth metal, alkali metal, hafnium, zirconium and thorium.

5. The process of claim 4 wherein the finely divided metal or colloidal metal is present in the catalyst in an atomic range of 0.01 to 5.

6. The process of claim 4 wherein the optional promoter element may be present in the catalyst in an atomic range of 0 to 5.

7. The process of claim 1 wherein the reducing agent is selected from the group consisting of hydrazine, hydrazine hydrate and a finely divided metal or colloidal metal.

8. The process of claim 7 wherein the finely divided metal or colloidal metal is tungsten.

9. The process of claim 4 wherein the phosphorus to vanadium atom ratio is 0.5:3 to 3:0.5.

10. The process of claim 4 wherein a and b are from 0.5 to 10.

11. The process of claim 1 wherein the compound containing pentavalent vanadium is vanadium pentoxide.

12. The process of claim 1 wherein the compound containing pentavalent phosphorus is phosphoric acid.

13. The process of claim 1 wherein the catalyst is prepared in the absence of a hydrogen halide, or an organic reducing agent.

14. The process of claim 13 wherein the organic reducing agent is an organic acid, aldehyde or secondary alcohol.

15. In a process for producing maleic anhydride from n-butane, n-butenes, 1,3-butadiene or a mixture thereof with molecular oxygen in the vapor phase at a reaction temperature of 250° C. to 600° C. in the presence of a catalyst comprising the mixed oxides of vanadium, phosphorus and uranium, the improvement wherein the catalyst is prepared by
(a) forming an aqueous oxide slurry of vanadium pentoxide;
(b) adding to said aqueous oxide slurry a mineral acid-free, inorganic reducing agent capable of reducing the vanadium in the vanadium pentoxide to a valence state below +5 to obtain an aqueous slurry containing reduced vanadium, wherein said reducing agent is selected from the group consisting of ammonia, hydrazine, hydrazine hydrate, a finely divided metal or colloidal metal;
(c) adding a uranium compound immediately before the addition of the reducing agent or after the addition of the reducing agent;
(d) adding phosphoric acid before the addition of the reducing agent or after the addition of the reducing agent;
(e) heating said aqueous oxide slurry under reflux conditions;
(f) removing the water from the resulting slurry to form a dried catalyst; and
(g) calcining said dried catalyst at a temperature of 250° C. to 600° C.

16. The process of claim 15 wherein the reducing agent is a finely divided metal or colloidal metal, hydrazine or hydrazine hydrate.

17. The process of claim 16 wherein the finely divided metal or colloidal metal is tungsten.

18. The process of claim 1 wherein the active catalytic material is coated on an inert support.

19. The process of claim 18 wherein the catalyst consists essentially of an inert support material having a diameter of at least 20 microns and an outer surface and a continuous coating of said active catalytic material strongly adhering to the outer surface of said support.

20. The process of claim 19 wherein the active catalytic material is about 10% to about 100% by weight of the inert support.

21. The process of claim 19 wherein the particle size of the inert support is 0.2 cms. to 2 cms.

* * * * *